United States Patent
Douglas et al.

(10) Patent No.: US 6,702,767 B1
(45) Date of Patent: Mar. 9, 2004

(54) MULTISENSORY STIMULATION SYSTEM AND METHOD

(76) Inventors: Nelson R. Douglas, 151 N. Alvardo Ave., Ojai, CA (US) 93023; Levy Zubin, 2150 Gridley Rd., Ojai, CA (US) 93023

( * ) Notice: Subject to any disclaimer, the term of this patent is extended or adjusted under 35 U.S.C. 154(b) by 0 days.

(21) Appl. No.: 09/961,678

(22) Filed: Sep. 25, 2001

(51) Int. Cl.$^7$ .................. A61H 33/14; A61G 10/00
(52) U.S. Cl. .................. 601/15; 601/16; 601/49; 601/70; 600/21; 600/28
(58) Field of Search .................. 601/15, 16, 18, 601/23, 47, 49, 50, 57, 70; 600/21, 26–28; 128/202.12, 205.26; 248/919, 923, 922; 386/30

(56) References Cited

U.S. PATENT DOCUMENTS

| | | | |
|---|---|---|---|
| 2,905,049 A | | 9/1959 | Laube |
| 3,628,829 A | | 12/1971 | Heilig |
| 3,826,250 A | * | 7/1974 | Adams .................. 601/16 |
| 4,603,030 A | | 7/1986 | McCarthy |
| 4,640,266 A | * | 2/1987 | Levy .................. 600/27 |
| 4,893,615 A | * | 1/1990 | Khabirova .................. 601/16 |
| 5,266,070 A | * | 11/1993 | Hagiwara et al. .......... 600/27 |
| 5,304,112 A | * | 4/1994 | Mrklas et al. ............. 600/27 |
| 5,610,674 A | | 3/1997 | Martin |
| 5,725,472 A | * | 3/1998 | Weathers .................. 600/21 |
| 6,169,595 B1 | | 1/2001 | Manne |
| 6,584,374 B2 | | 6/2003 | Lee et al. |

* cited by examiner

Primary Examiner—Danton D. DeMille
(74) Attorney, Agent, or Firm—Dowell & Dowell, P.C.

(57) ABSTRACT

A multisensory stimulation system and method of use. The system includes a housing articulate on a support so as to align a marked viewport with an individual. The housing defines a viewing chamber which is an extension of a reflective light and image optical system chamber which receives light and images from one or more video monitors or images projectors and, in some embodiments, from alternate sources such as black lights and strobe light devices. The system also includes an aromatic sensory component, tactile sensation devices, an audio input system, and audio delivery devices.

32 Claims, 10 Drawing Sheets

MULTISENSORY STIMULATION SYSTEM AND METHOD

BACKGROUND OF THE INVENTION

1. Field of the Invention

This invention is generally directed to systems and methods for stimulating sensory perceptions including visual, aural, olfactory and tactile senses for purposes of mental and physical stimulation and therapy, relaxation and entertainment. The invention is further directed to multisensory systems for stimulating visual, audio and olfactory senses through enhanced visual presentations, monitored and selected audio inputs and monitored and selected olfactory inputs.

2. Brief Description of the Related Art

Systems have been created for purposes of sensory stimulation not only for enhanced entertainment reasons but for purposes of therapy for the release of stress as well as to improve body functioning. Other concepts with respect to sensory stimulation have dealt with creating enhanced visual system displays, audio variations and/or olfactory inputs to create different moods for one or more persons subjected to such systems. By way of example, in the entertainment industry, basic visual systems have been modified to create three dimensional imagining to make visual presentations more realistic. Other variations of image projection include creating multiple lighting and strobing effects of image presentation in order to stimulate an individual's mind as it is responses to different colors, shades, light intensities and sequences, all for purposes of stimulating an individual's response to what is visually perceived.

As with changes in visual stimuli, changes in audio stimuli can also have an effect on an individual's feelings, mood and health. Dynamic audio presentations tend to increase heart rate and biorhythm functioning whereas more melodic softer or quieter audio presentations tend to create a soothing effect on individuals.

By combining different audio programming with visual presentations, the movie industry has attempted to change the manner in which people become involved while viewing a film. In some prior art presentations it has been proposed to provide aromatic essences which are released into a theater to combine with the visual and audio presentations to achieve yet a higher degree of individual involvement with the presentation of a film. A further stimulation includes providing movement or vibration of seats in theaters to further stimulate the individual through a sense of touch or through a sense of bodily orientation which changes as the visual and audio presentations change. By combining numerous sensory inputs a heightened interaction can be established between individuals and a programmed presentation.

To date, however, most multifaceted sensory stimulation systems have been provided in the entertainment industry for purposes of stimulating the senses of an audience. Such systems are not only costly and complex, they are also not adequate for use with specific individuals. Thus, there is a need to provide individualized sensory stimulation systems which utilize multiple sensory inputs which can be varied according to an individual and to an individuals response to such stimulation. Such sensory stimulation systems can be used not only for purposes of entertainment but, more importantly, for purposes of mental and physical therapy to reduce stress, relieve headaches, including in migraine cases, reduce tension to relieve high blood pressure, to alter moods in order to create a more beneficial and alert mental status for a given individual and/or for purposes of relaxation, mind stimulation and the like, all which can have a positive mental and physical effect on an individual.

SUMMARY OF THE INVENTION

The present invention is directed to a multisensory stimulation system and method of use of such a system which is specifically designed to overcome the shortcomings of prior art stimulation systems and which is particularly adapted for individualizing sensory stimulation. The system includes a primary housing which is articulated on a support so as to be selectively alignable with an individual who is seated relative to the housing. In a preferred embodiment, the individual is seated on a contoured reclined seating device so that the individual is physically relaxed when the system is in use. In some embodiments, the seating device may be provided with heat exchange elements to supplement sensory stimulation through heat and cold therapy or the seating device may be provided with vibrating transducers or other devices for tactile purposes or for adding massage therapy and stimulating sensory touch response for an individual when using the system of the invention. Although not disclosed in the preferred embodiment shown in the drawings, further modifications could be made to the system such as to reorient the seating device and/or the sensory stimulation system to generate further sensory responses of an individual during the use of the system of the invention.

The housing is designed with a viewport generally at one end thereof which viewport is designed such that an individual's eyes, nose and ears are generally directed into the housing and so that ambient light, sound and the like does not effect the individual. The viewport communicates visually with a main optical assembly mounted within the housing. The main optical assembly includes a plurality of reflective surfaces which are used to reflect light and images in a plurality of patterns to create varied visual effects. Light and images entering the main optical assembly are provided by one or more monitors or image projectors which are also mounted to the housing. Such monitors may be computer controlled monitors allowing presentation of specific programming from a data base or disc. Both preprogrammed and updated programming can be used to optimize the efforts of sensory stimulation for each individual utilizing the sensory stimulation system. In some embodiments, the monitor may be in the form of image projectors including television screens with are connected to an appropriate video input such as a video cassette, CD or DVD player so that prerecorded visual programs can be played through the monitor to an individual using the system.

The monitor is mounted on a frame within the housing so that the light and images therefrom are directed into the main optical assembly such that the light and images must be reflected from a plurality of reflecting surfaces before being transmitted for viewing to the viewport. This multi-reflection of light and images within the main optical assembly creates a three dimensional and floating effect to the images viewed within the housing.

To further change the visual characteristics of any program being presented by the internal monitor, secondary light sources and light controllers may be mounted to the housing and allowed to communicate within the main optical assembly to create secondary images or light patterns which border the primary or main images issuing from the monitor. The secondary optics one separately attached to one of the exterior panels of the main optical assembly and communicate through an optical lens port in which a Fresnel lens is mounted. An inlet end of the secondary optical assembly is in open communication with a portion of the screen of the monitor which is not utilized to create the main or primary image display. In this respect, the monitor screen is mounted such that only a portion of the monitor screen is communicated directly into the main optical assembly such that portions around the perimeter of the main screen or image display are not communicated directly into the main optical assembly but are available for transmission into the main optical assembly after passing through one or more of the secondary optical assemblies.

In the embodiment disclosed in the invention a single secondary optical assembly will be disclosed, however, it should be noted that a plurality of such assemblies may be used in accordance with the teachings of the present invention.

The inlet end of each secondary optical assembly communicates with a portion, normally an exterior or corner portion, of the monitor such that light from such portion enters a reflective interior of a secondary housing. A portion of one sidewall of the housing includes a shutter which is mirrored on its inner surface so as to form a reflective surface when the shutter is closed with respect the sidewall of the secondary housing. When the shutter is opened, a light source mounted exteriorly thereof can be used to direct light or pulses of light into the secondary housing and toward the Fresnel lens which is generally mounted at an angle relative to a primary axis of light coming from the monitor. An end portion of the secondary housing includes a plurality of angled mirrored surfaces for further reflecting light coming from the monitor at an angle toward and through the Fresnel lens. Therefore, the interior of the housing of the secondary optics assembly forms a mirrored tunnel extending between border portions of the monitor to the Fresnel lens.

The primary light source associated with the use of a shutter assembly is a blacklight source which is mounted in front of a reflector which directs the blacklight towards the Fresnel lens when the shutter is opened, such as by a servo or a solenoid mechanism which can be regulated in its timing sequences to pulse or slowly open and close the shutter to allow the blacklight to pass through the Fresnel lens into the main optical assembly. The blacklight is used to make visible flourescent lacquered images which are selectively applied on the reflective or mirrored surfaces on the interior of the main optical assembly. Under normal conditions and with the shutter closed such flourescent lacquered images can not be seen, however, upon opening of the shutter and activation of the blacklight source, the images become brilliant and are reflected off the additional reflective surfaces within the main optical assembly.

A further effect may be achieved by also mounting a strobe light adjacent the shutter and exteriorly of the mirrored tunnel of the secondary optic system. In this manner, when the shutter is opened, the strobe lighting may also be introduced into the main optical assembly through the Fresnel lens.

In the preferred embodiment, the Fresnel lens is convex from or toward the main optical assembly.

The system also incorporates audio speakers which are mounted adjacent the mask or headphones through which different audio outputs can be provided from essentially any exterior source of audio supply such as a conventional tape or disk player amplifier or the like. In addition, sounds can be routed through or from a computer or Digital Signal Processor (DSP) to create computer generated or enhanced sounds that can be varied to obtain different audio responses impressions to an individual utilizing the sensory stimulation system of the invention.

A further component of the sensory stimulation system of the invention is an aroma control system. The aroma system includes a plurality of essence containers which are mounted within the main housing. One or more pumps are provided to direct pressurized air through inlet tubes into the essences containers. Outlet tubes carry essences which have been defused or entrained into the air flow from the pumps toward a venturi which is mounted adjacent to the mask of the housing. The tubes extending from the essence bottles to the venturi are directed with at least some vertical component when the housing is in its normal use position such that any condensed essence returns to the essence containers or bottles by gravity.

The venturi communicates with a source of fresh air supply which includes a pre-filter and fan assembly which conducts outside fresh air toward the center of the venturi and toward an evacuation outlet provided in a collar portion of the mask. In this respect, the fresh air is directed through the venturi and entrains the aroma from the essence bottles therein through the activation of pressure actuated valves mounted adjacent to the venturi. In some embodiments, separate pumps will be interfaced with the essence bottles as opposed to a single pump and a plurality of valves. The fresh air having the essences entrained therein is thereafter generated across the face of an individual so as to be easily included before the air is positively evacuated from the housing. In the preferred embodiment, the air enters an evacuation outlet adjacent the mark where the air passes through a filter in which any exiting aromatics are removed before the air is discharged to the ambient environment. The pumps which provide air through various inlet lines to the essences bottles are controlled utilizing valves operable in response either to manual input or to a computer controller such that the different essences can be supplied either by a predetermined program, by continuously upgrading a program if reactions of a person are being monitored and inputted as they experience the sensory stimulation system or manually controlled by a separate operator.

The sensory stimulation system of the invention further includes an exhaust fan mounted adjacent the monitor which draws cooling air past the monitor and discharges it on an opposite side of the housing from the viewport.

Control of the various elements of the invention may be accomplished manually through a control panel mounted to one side of the housing. In some embodiments computer actuated controls may be utilized to create an interaction delivery system such that pre-programming may be updated or changed depending upon a person's responses. Responses may be based on biofeedback sensors, voice recognition devices, or other conscious or subconscious inputs to thereby enhance sensory simulation utilizing a variety of visual, audio and olfactory sensory actuators.

Utilizing the methodology of the present invention, an individual is initially seated on a chair in a somewhat reclined position after which an operator pivots the main housing on its support pedestal so that a mask at one end thereof is positioned in surrounding relationship with the individual's face. One or more handles may be provided for manipulation by the individual or an operator to ensure comfortable positioning of the mask and housing relative to the individual.

To stimulate the various senses, once the mask is correctly positioned, the programmer, a pre-programmed computer or a media playback device using pre-recorded media may be activated to control various sensory stimulation elements of the invention. By initially activating the visual input monitor, images are reflected off the multi-faceted mirror-like inner surface of the main optical assembly. Depending upon the types of images being projected or reflected, different responses are induced in the individual using the system. To further enhance the system, the secondary optics systems may be activated in which case the shutter associated with each secondary system is opened allowing the blacklight source to illuminate fluorescent areas which have been pre-applied to the various reflective surfaces within the main optical assembly such that additional reflective elements appear within the space of the primary optical assembly. As previously mentioned strobe lighting may also be introduced through the secondary optical assemblies at this time.

During the visual display further sensory stimulation may be affected by activation of the speakers or headphones through input from a sound system and activation of the aroma system may be accomplished either manually, by pre-programmed computer input or by playback of prerecorded media queues. When the aroma system is activated, pressurized air will be directed from the pumps through selected ports so that the air is directed to predetermined essence containers or bottles mounted within the housing. The essences entrained in the incoming pressurized air then pass upwardly through discharge conduits to a venturi mounted interiorly of the housing and upstream of the primary optical assembly and viewport or mask. A fresh air stream is introduced through the throat of the venturi and will open injection valves associated with the discharge conduits from the aroma assembly thereby entraining the various aroma essences within the air flow which then passes through the primary optical assembly and in close proximity to an individual so that the aromas can be inhaled prior to being evacuated through evacuation opening in a collar of the mask.

It is the primary object of the present invention to provide a multisensory stimulation system and method for use of such a system which allows an individual to be subjected to selected combinations of visual, audio, olfactory and other stimulates and wherein the visual inputs may be varied by the use of primary and secondary optic systems.

It is also an object of the present invention to provide a multisensory stimulation system which can be utilized not only as an entertainment device but also as a therapeutical device wherein changes in visual, aural, olfactory, tactile and other stimulates can be used singularly or in various combinations to effect beneficial mental and physical response for an individual using the system.

It is also an object of the present invention to provide a multisensory stimulation system and method wherein the system can be adjusted to suit substantially any individual and wherein the system may be controlled either by a separate operator, by pre-programmed inputs or by interaction feedback or combinations thereof in order to achieve optimal stimulation response for each individual.

It is yet a further object of the present invention to provide a multisensory stimulation system which includes both primary and secondary image displays such that the secondary images can be activated independently of the primary images thereby causing a unique and exciting interaction therebetween wherein images that are reflected into a main optical chamber from either the primary or secondary systems will appear to float in infinite space or on different planes forming uniquely perceived patterns of a visual environment as viewed by an individual using the system.

BRIEF DESCRIPTION OF THE DRAWINGS

A better understanding of the invention will be had with respect to the drawing figures wherein.

DESCRIPTION OF THE PREFERRED EMBODIMENT

Figure 3:
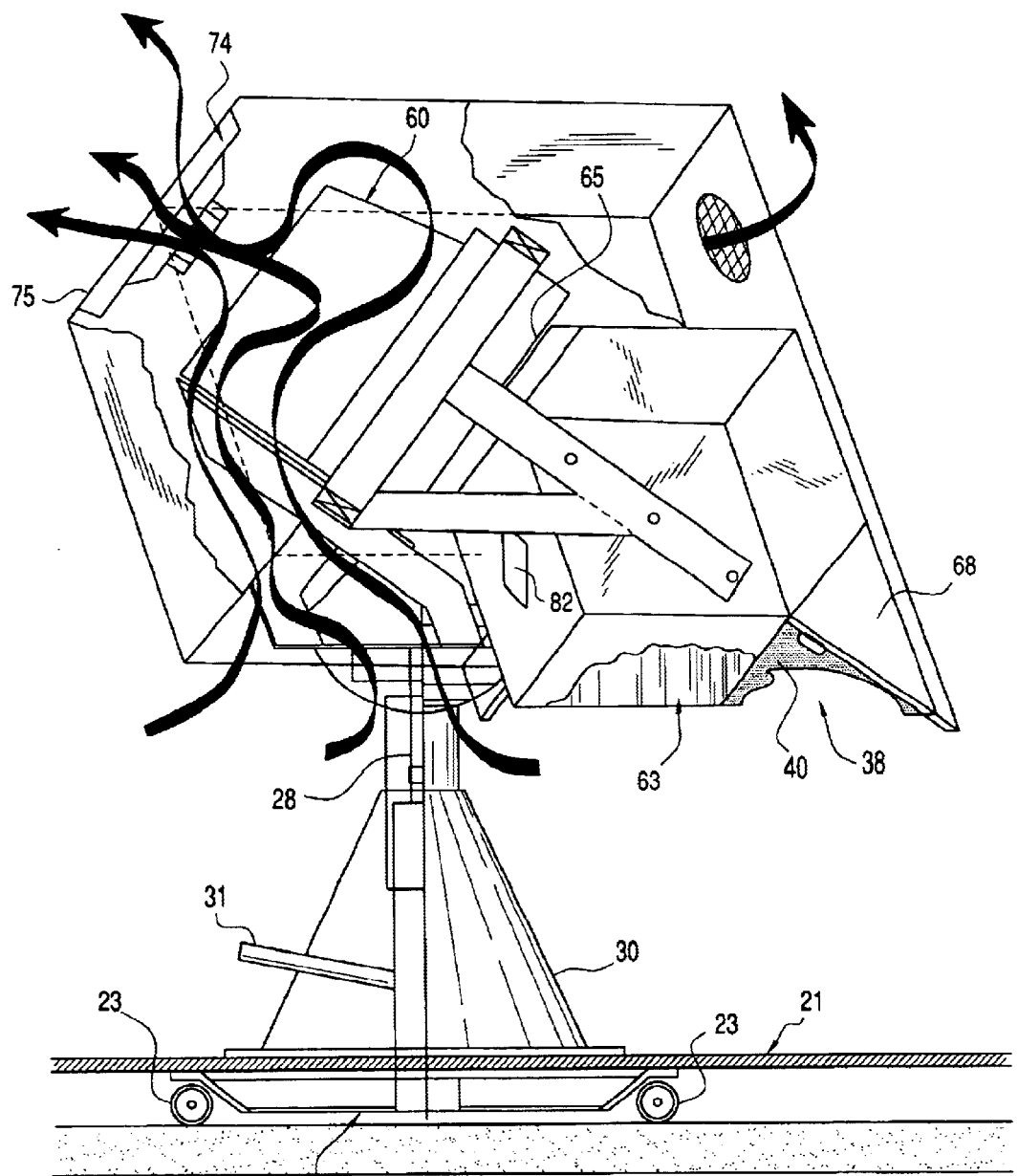
FIG. 3 is a partial cross-sectional view of the apparatus of FIGS. 1–3 showing a display and primary optics assembly of the invention which is mounted within the housing shown in FIGS. 1 and 2.

With continued reference to the drawing figures, the multisensory stimulation apparatus and system 20 of the invention is shown including a base or platform 21 which is designed to be maneuverable and, as shown in FIG. 3, may be mounted on a dolly assembly 22 including support wheels 23. The platform 21 supports a seating device 25 which in the preferred embodiment shown includes a chair having a reclined seat for supporting a person "P" in a position to receive multisensory inputs from the apparatus.

Figure 1:
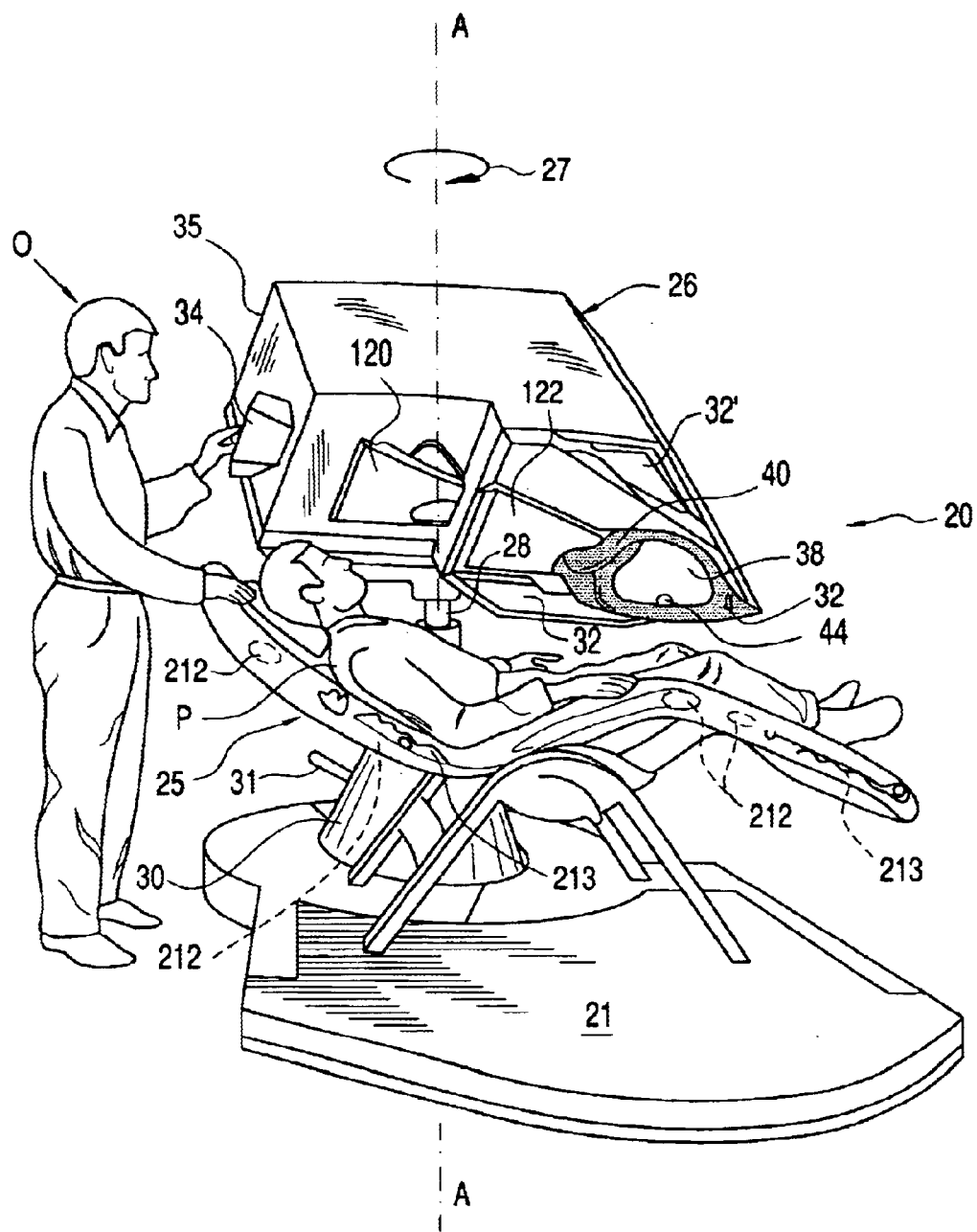
FIG. 1 is a perspective illustrational view of a preferred embodiment of multisensory stimulation apparatus of the invention in a loading position showing a movable platform supporting a chair on which a user of the system is seated and an operator for controlling operation of the system which is mounted within a movable housing pivoted to a support pedestal.

In FIG. 1, the person "P" is shown as being seated in a reclined position from the seat 25 relative to a housing 26 in which the multisensory components of the invention are housed. The housing 26 is rotatably supported about a vertical axis "A—A" as shown by the arrow 27 in FIG. 1. The housing is supported on a support post or ram 28 which is vertically adjustable with respect to a pedestal 30 by way of an operating lever 31 so that the height of the housing 26 may be selectively adjusted to appropriately aligned with a person "P" seated within the seating device or chair 25.

Figure 2:
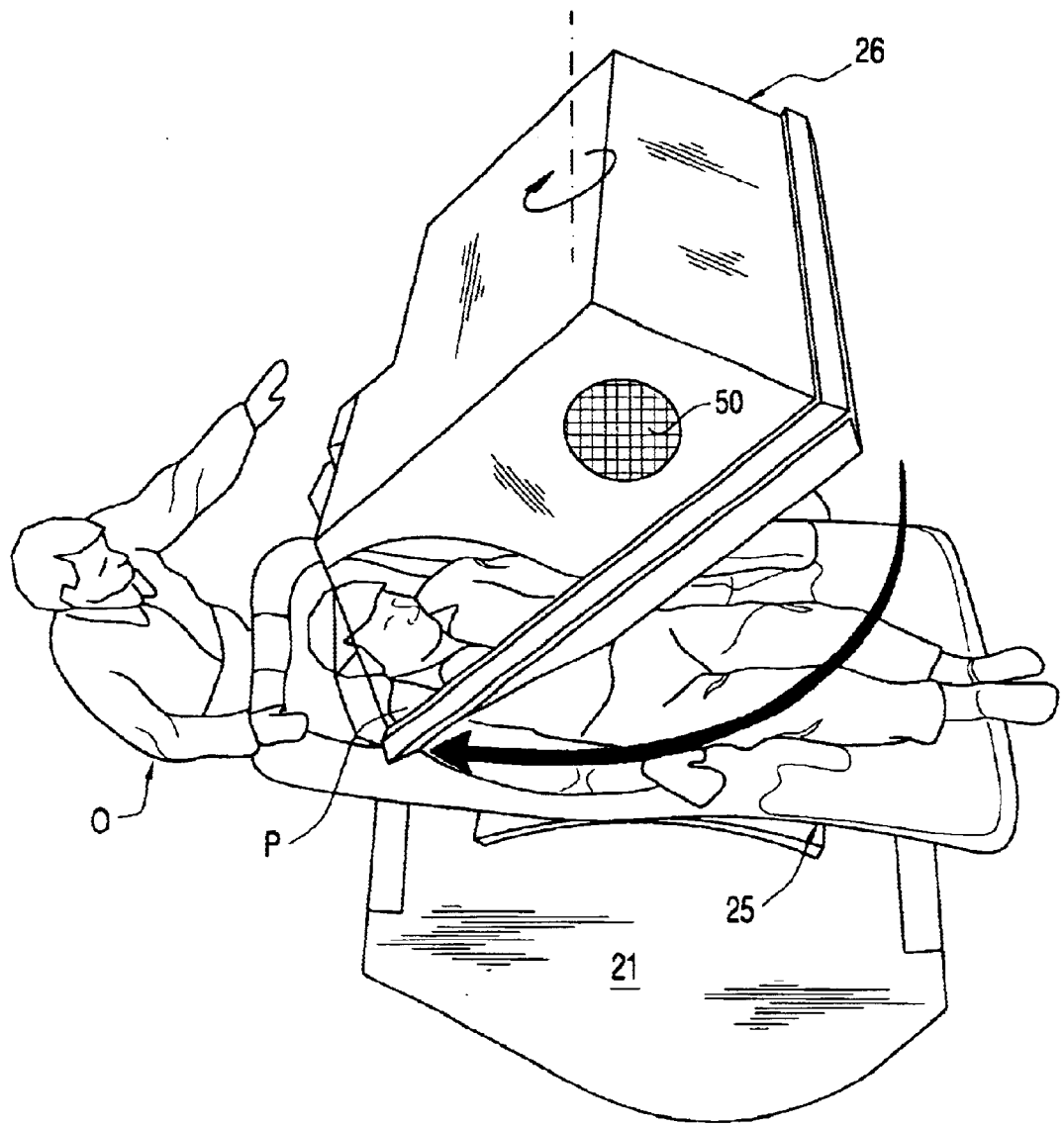
FIG. 2 is a view similar to FIG. 1 showing the housing being pivoted into operable relationship with respect to an individual receiving multisensory stimulation having portions broken away.

As shown in FIGS. 1 and 2, the multisensory stimulation apparatus and system may be controlled by an operator "O" who has access to a control panel 34 mounted to a rear wall 35 of the housing.

In the position of the housing shown in FIG. 1, the housing is offset with respect to the chair so that the person "P" may have easy ingress and egress with respect thereto. After a person is seated, the housing is pivoted about the axis "A—A" such that a viewport 38 into the housing is aligned over the face of the person, as shown in FIG. 2 through the cut-away in the drawing figure. The housing may be pivoted by the operator "O" by manipulation of a handle 32' or, in some embodiments, the housing may be pivoted by the person "P" by engaging one or both of two handles 32 mounted to the housing, see also FIG. 7. Surrounding the viewport 38 is a soft generally annular mask 40 which is cushioned so as to protect the face of the individual from accidental injury and which also blocks out ambient light and sounds. The mask is preferably designed to minimize outside interference and distraction so that the eyes, ears and nose of the individual are essentially blocked from ambient conditions and are subject only to conditions of sensory stimulation as will be provided in the area of the viewport 38 during the operation of the system. The mask is preferably matte black to prevent light from reflecting upon it and thus entering the viewport, and is ideally made of sound absorbent material to reduce sound reflection.

Figure 7:
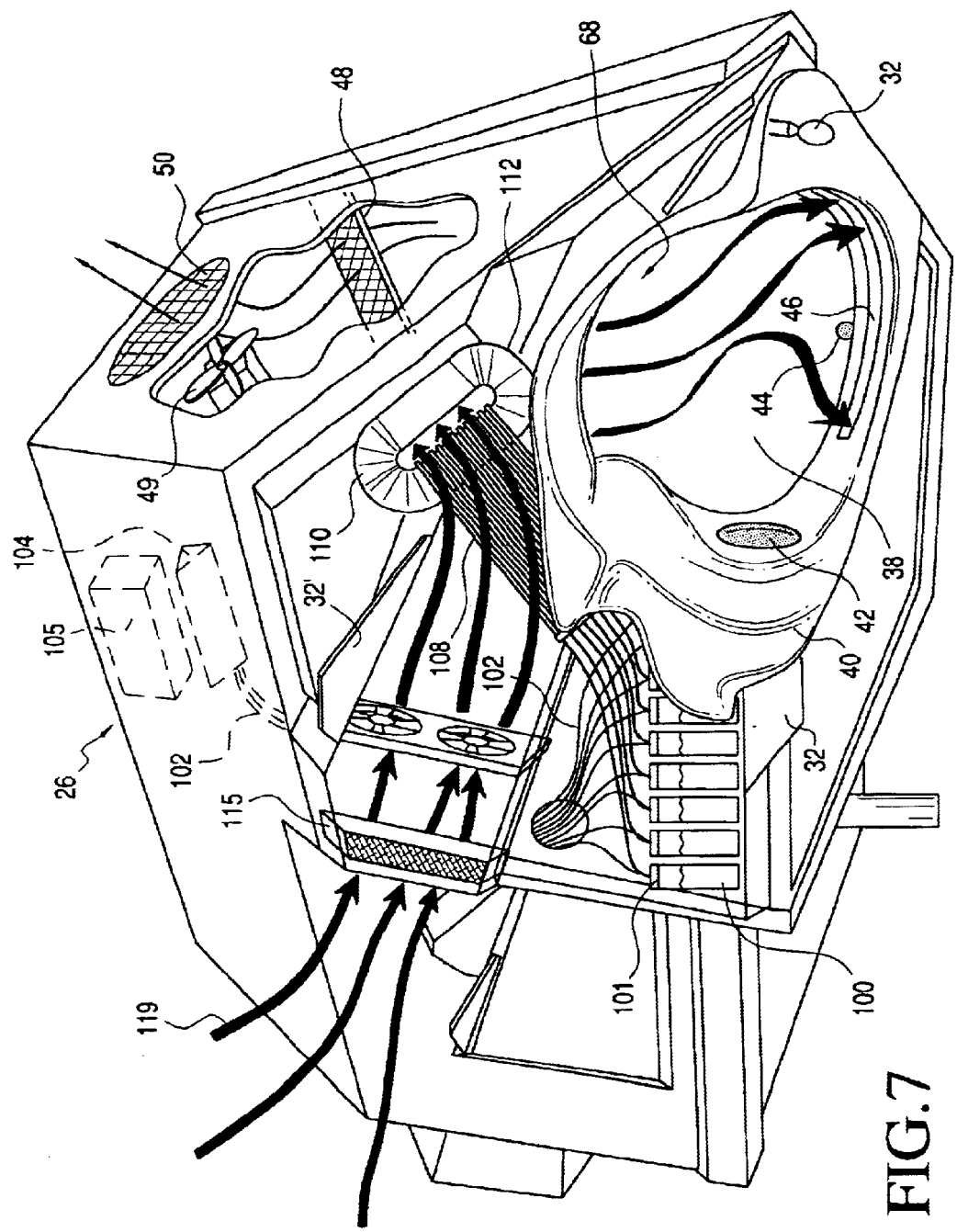
FIG. 7 is a partial cross-sectional view through the housing of the invention and showing an aroma system of the invention.

With specific reference to FIG. 7, a more detailed showing of the soft mask 40 is shown surrounding the open viewport 38. Mounted on opposite sides of the mask are audio speakers 42 (only one being shown in the drawing figure). The audio speakers 42 are electrically connected to an appropriate sound source such as a personal computer, CD player, radio, or other audio amplifier for purposes of receiving sound programming to provide for audio sensory inputs to the person "P" seated on the chair 25. As opposed to, or in addition, headphones may be used for audio stimulation. Also mounted adjacent the mask is a microphone 44 by way of which the person seated in the chair may speak either to an operator "O" or to a voice recognition system associated with a computer controller for the multisensory delivery system. The person's voice can be used for analysis, such as stress level, or may be routed to a computer or DSP to create altered sounds, chair vibrations or visual imagery that is synchronized to the voice. As an example, a person might sing a song, hear it in 3-D with a new voice or echoes, while feeling chair vibrations moving through his or her body, and watching images of color and light appearing and transforming in their visual space.

Also provided in the area of the mask is an elongated exhaust port 46 through which air from the interior of the housing is drawn and passes through a forward portion of the housing through a filter 48 by way of an exhaust fan 49 which is mounted to direct airflow outwardly through an exhaust port 50 into the ambient environment. The exhaust system is particularly provided for use in purifying airflow leaving the housing which airflow may include entrained aromatics or essences as will be described hereinafter. The filter 48 is used to withdraw any aromatics before the air is discharged through the discharge port 50.

Figure 4:
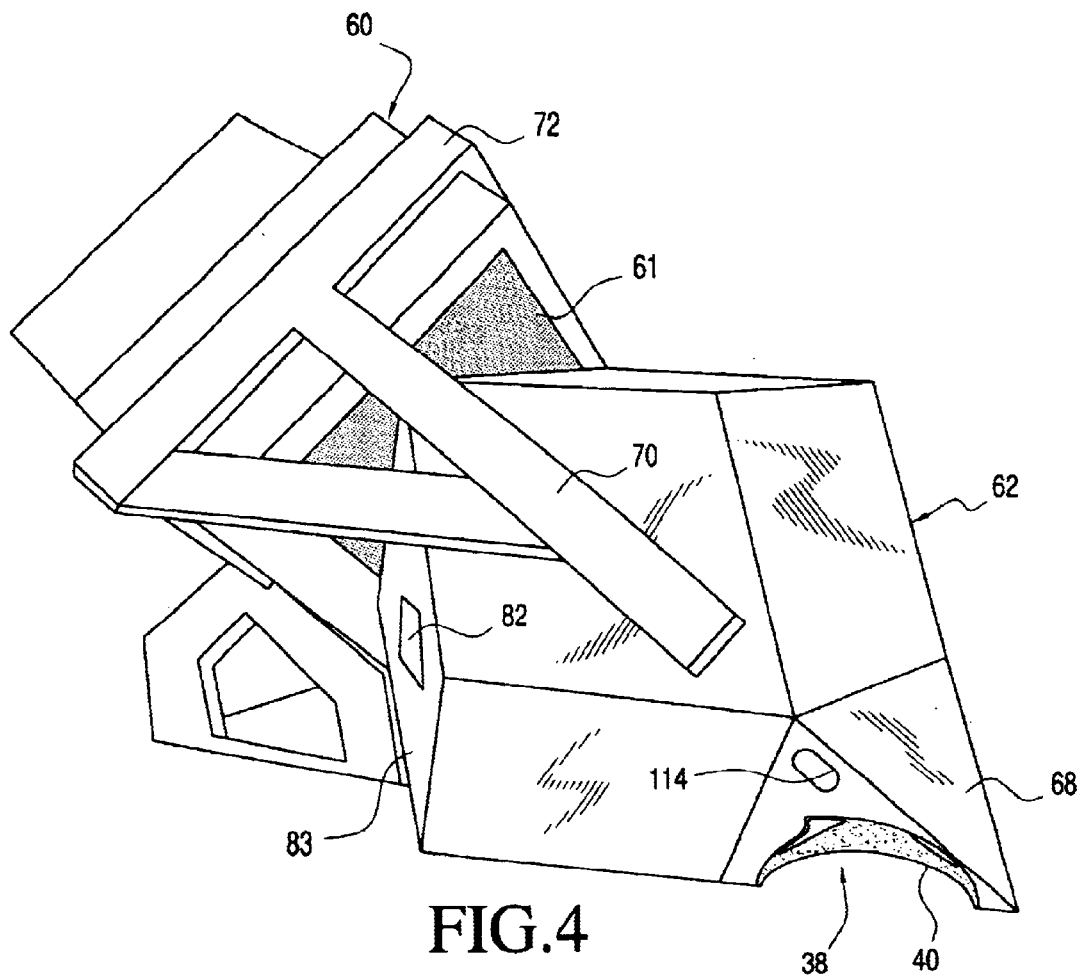
FIG. 4 is a perspective view of the display and primary optics assembly of the invention showing the primary optical assembly in relationship with respect to a monitor for directing images therein.

As previously discussed, the multisensory stimulation system and apparatus of the present invention is specifically designed to provide a plurality of stimuli to an individual. These include visual, audio, olfactory and perhaps senses of touch or feel. A visual stimulation is provided by providing light from an image input or video monitor 60 having a display screen 61 which is mounted so as to project a portion of an image from the display screen into the interior of a primary reflection chamber which is formed of multiple inwardly reflecting panels. The monitor and display assembly is particularly shown in FIGS. 3 and 4. The primary optical display chamber is designated at 62 and includes a plurality of intersecting angularly related wall segments having mirrored inner surfaces which reflect light and images into an open area 63 within the chamber 62, as shown in FIG. 3. The cutaway in FIG. 3 also shows the mirrored inner surfaces of the walls defining the primary reflective chamber and of the primary optical system. In the preferred embodiment, the primary optical chamber is formed as an extended rhombic dodecahedron which is generally a twelve sided figure. As shown, a portion of one end of the chamber has been cutaway to form an opening 65 which abuts a central portion of the display screen 61, as shown in FIG. 4, to thereby allow the entry of light and images into the interior of the primary optical or reflective chamber. The opposite end of the chamber includes an opening into a reflective viewing chamber 68 which aligns with the viewport 38 defined centrally of the mask 40. The inner walls of the viewing chamber are also reflective and receive light which has been reflected from the surfaces of the interior of the primary optical chamber and also some light which passes directly thereto from the display screen 61. In this manner, a combination of reflected and direct lighting is viewed by an individual or person as they look into the viewing chamber. The multifaceted reflective surfaces create images that appear to float and change in space and thus give a great deal of depth and illusion as well as changing light patterns to objects to being viewed. By changing the images, light patterns, colors and other visual characteristics of the display, different stimulative responses can be obtained from to a person viewing the images in the viewing chamber.

The primary optical assembly 62 is mounted to spaced arms 70 of a frame 72 which surrounds the monitor and display screen 60 and 61. The housing 26 is fixedly mounted about the frame 72.

With specific reference to FIG. 3, whenever the monitor is operated, cooling air is drawn through the housing by way of a cooling fan 74 mounted along one of the back walls 75 of the housing. Air enters the housing through a lower portion thereof following the path shown by the arrows in FIG. 3 so as to convey heat from the monitor outwardly of the housing. Appropriate controls are connected to both the cooling fan 74 and the monitor 60 to ensure that whenever the monitor is turned on the cooling fan 74 is also activated to exhaust air from the housing.

The monitor 60 may be a conventional television monitor or may be a computer monitor or other light or image projector. In this respect, the monitor 60 may be connected to an appropriate control device as will be discussed hereinafter by way of which a variety of video inputs can be transmitted thereto. The video inputs may be supplied by a computer or from a VCR, video disk or DVD disk player. The video inputs to the monitor 60 may be preprogrammed such as by inputting pre-recorded visual images on a CD or DVD disk or, the video input may be continuously updated or altered depending upon inputs received by a person undergoing sensory stimulation.

Figure 12:
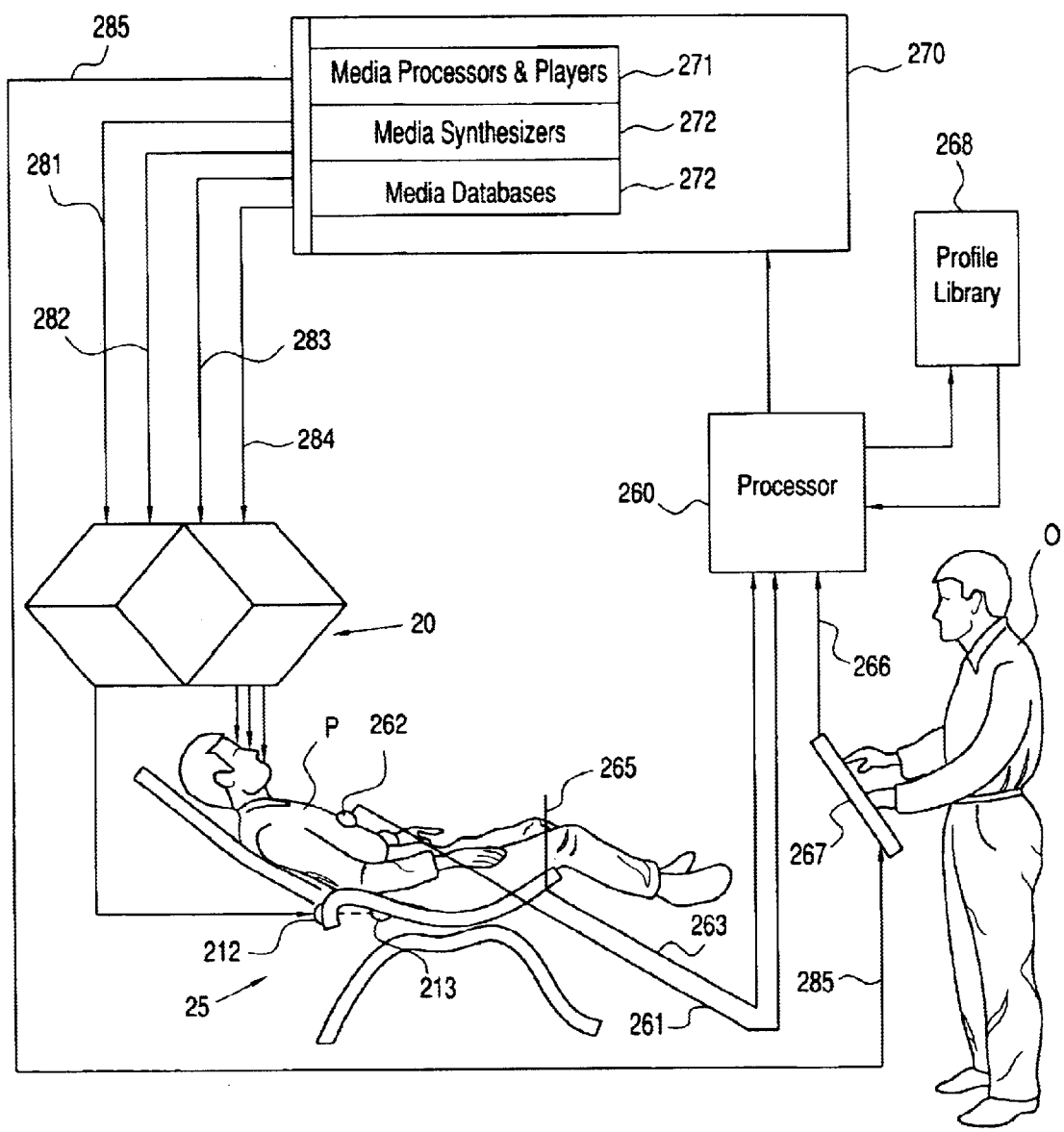
FIG. 12 is an illustrational diagram of an interactive control system of the invention.

With respect to the foregoing, the present invention provides for interactive changes with respect to sensory stimulation. As shown in FIG. 12, an individual may be monitored in order to determine what effects and responses a person undergoes in response to presented sensory stimulation. By way of example, the present invention may be used in cooperation with a biofeedback system wherein sensors, such as EEG or brainwave sensors, are applied to the person undergoing stimulation so as to provide feedback information with respect to body temperature, pulse rate, skin moisture, blood pressure and related bodily functioning. The sensors may be individually placed on the person before they receive sensory stimulation or some sensors may be incorporated into the seating device. In this respect, sensors may be placed along the arms of the seating device so as to be engageable with palm and fingers of an individual's hand whereby various bodily functions can be easily monitored. The information being monitored can be inputted to a computer system so that the information being received can be utilized to change programming of the visual as well as audio, olfactory or other sensory inputs used with the invention. In addition to the foregoing, the computer may also be connected to a profile or personal library which records the responses of an individual undergoing sensory stimulation. The profile or personal library can be continuously updated to enhance and to calibrate future sensory experiences.

In addition to the primary optical display assembly 62, a secondary optical source or assembly may be secured adjacent to the primary optical assembly and communicate therewith in order to supply secondary images and light patterns into the primary optical display assembly. Images that are reflected from the secondary optical assembly into the primary optical chamber will appear to float in infinite space or on different planes transforming a perceived configuration of the overall environment being viewed in the viewing chamber.

Figure 5:
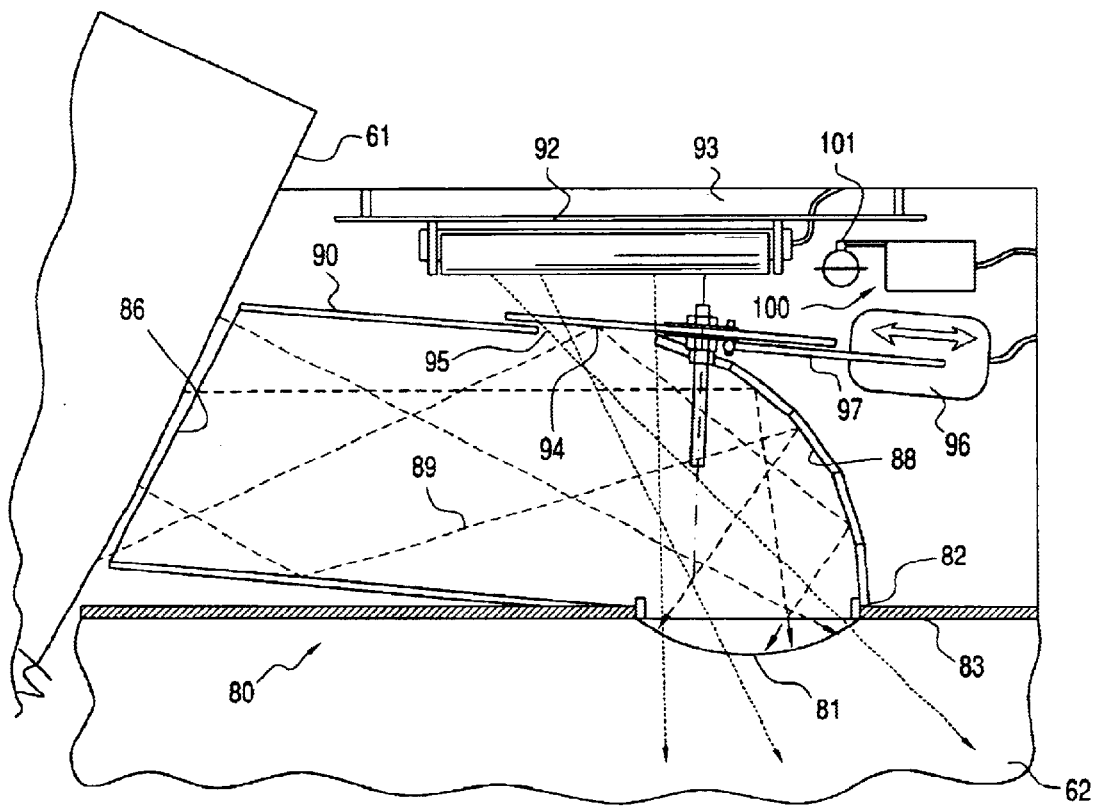
FIG. 5 is a partial cross-sectional view through a secondary optics assembly which may be utilized with the invention.
Figure 6:
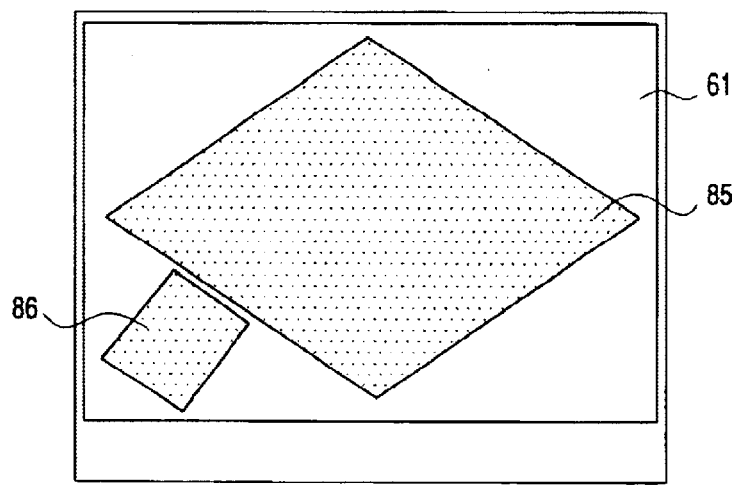
FIG. 6 is an image projection showing where the input from a monitor is used to direct images into either the primary or secondary optics assemblies of the invention.

The secondary optical assembly is designed to be mounted to supply secondary light and images through a viewport 82 provided in one of the walls of the primary optical display housing 62. The panel or wall in which the viewport is provided is shown in FIG. 4 as being designated as 83. With specific reference to FIG. 5, the secondary optical display assembly 80 is shown in greater detail. The display assembly includes an output Fresnel lens 81 of a size to be mounted within the lens port 82 in the panel 83 of the primary optical housing 62. Light and images pass through the Fresnel lens into the primary optical display chamber by way of being transmitted from a portion of the monitor display screen 61 which falls outside of the portion of the display screen which transmit light and images directly into the primary optical display assembly. In this respect, and as shown in FIG. 6, the display screen 61 provides a central source of light and images as exemplified by the area 85. The portion of the display screen 61 surrounding the area 85 may be used as a secondary source of light and images for one or a plurality of secondary optical display assemblies. As shown, an area 86 is shown which is aligned with the secondary optical display assembly 80 of FIG. 5. The optical display assembly is shown only in cross section in FIG. 5 and may be substantially of any cross sectional configuration provided that the inner surfaces are reflective. In this respect, the secondary optical chamber forms somewhat of a tunnel having an end portion having a plurality of multifaceted angled surfaces as shown at 88 for redirecting light beams 89 toward the Fresnel lens 81 so the light passes into the primary optical display chamber after passing through the lens 81. The tunnel configuration is generally defined by reference 90.

In order to provide additional optical effects, the present invention also incorporates supplemental light sources. In this respect, and as shown in FIG. 5, a secondary source of light such as a blacklight 92 is mounted within a chamber 93 exteriorly of the secondary reflective tunnel 90. The secondary light source is connected to a control assembly as will be discussed in greater detail and is activated upon the opening of a slide shutter mechanism 94 which covers an opening 95 in a side portion of the tunnel 90. The shutter is controlled by a servo or other actuation member 96 which is also electrically connected to a control assembly. The solenoid or other mechanism includes a rod 97 connected to the shutter 95 and when activated is effective to open the shutter 94 relative to the opening 95 in the sidewall 90 of the tunnel. Simultaneously, the blacklight 92 is activated and thereby directs blacklight waves into the primary optical chamber through the Fresnel lens 81.

In accordance with the teachings of the present invention, various internal portions of the primary optical chamber may be pre-treated with flourescent type materials which only become visible upon activation with a blacklight source. Therefore, whenever the blacklight source is activated different flourescent images will also appear and be reflected throughout the other images and light patterns being created and being reflected through the primary optical chamber and thus will be viewable by a person viewing the interior through the viewing chamber.

To create additional light patterns, a strobe light assembly 100 may also be provided within the chamber 93. The strobe light 101 may be pulsed or activated whenever the shutter 94 is opened relative to the opening 95 by selective control of a control mechanism as will be discussed hereinafter. The additional pulsation of visible light will create a further visual stimulation for a person viewing the images and light patterns within the viewing chamber. Upon closure of the shutter 94 both the strobe light and the blacklight will be deactivated. Access to the supplemental light sources is through a panel 120 in the housing 26.

As previously mentioned, although only a single secondary optical assembly is shown in the drawing figures a plurality of such assemblies may be mounted adjacent to the primary optical assembly and communicate therewith through appropriate lens ports such as the one shown at 82 in the drawing figures.

Although not shown in the drawing figures, it is possible to time or sequence the visual effects presented to the primary optical chamber and viewable through the viewport by controlling the monitor and secondary light sources so as to be controlled by an audio input. By appropriate amplification, filtering and/or processing the audio and visual sensory displays can be appropriately correlated.

The present invention also provides for olfactory stimulation by allowing one or more of a plurality of essences, such as appropriate oil essences, to be entrained in a supply of air which is directed to the viewing chamber and which passes adjacent to the mask 40 as previously described, so that various selected essences or aromatics may be sensed by the person seated adjacent to the multisensory stimulation apparatus 20.

Figure 8:
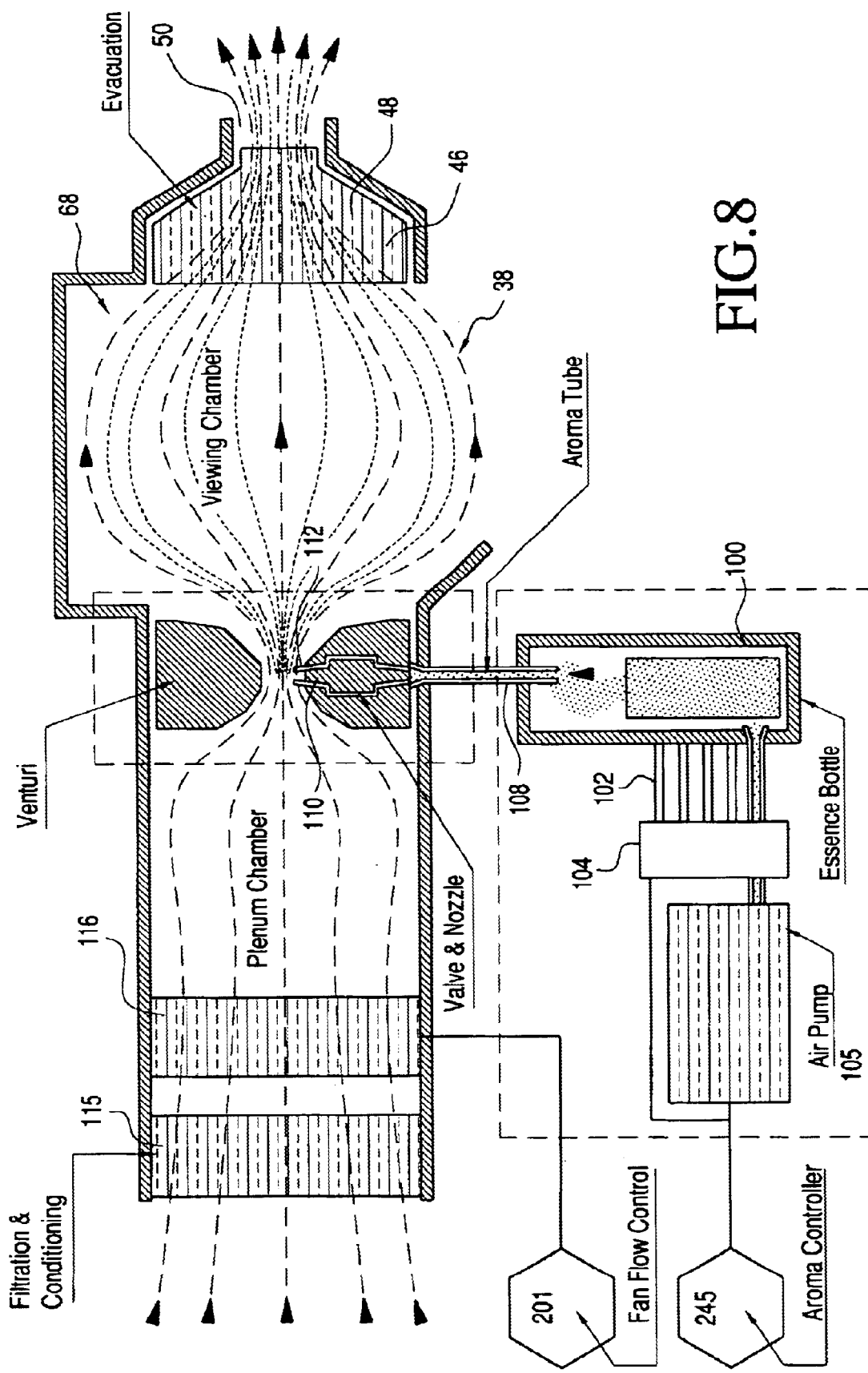
FIG. 8 is a schematic operational diagram of the aroma delivery system of the invention.

With particular reference to FIGS. 7 and 8, the aromatic supply system of the invention will be disclosed in greater detail. A plurality of containers 100 are mounted within the housing and are filled with essence oils or other aromatics generally in the form of liquids. Each container has a top closure 101 through which an air inlet line 102 extends. The inlet lines extend from a distribution header 104 mounted within an upper portion of the housing 26 which header includes a plurality of valves (not shown) for selectively connecting various of the inlet lines 102 with selected essence containers 100. Pressurized air is provided to the distribution header 104 by suitable fan or pump 105 also mounted within the upper portion of the housing 26. A controller 245, as shown in FIG. 8, is electrically connected to the distribution header 104 and the pump 105 and is controllable to selectively operate one of valves associated with one of the air input lines 102. From each of the containers 100 aromatic exhaust lines 108 extend upwardly through the lids 101 to a plurality of injection valves 110 mounted in the throat of a venturi 112 which is mounted so as to form an opening into the viewing chamber. The opening in which the venturi is seated is formed generally at 114 in drawing FIG. 4. The valves, are open due to pressure of pressurized air within the aromatic exhaust lines 108 and serve to inject pressurized air having essence oils entrained therein into the throat of the venturi 112 as ventilation air is drawn through a prefilter 115 mounted within the housing upstream of a fan assembly 116.

As opposed to using separate valves for connecting the inlet lines 102 with the containers 100, a plurality of pumps may be used with each pump connected to supply airflow to a container. The pumps, or valves, may be controlled to operate in cooperation with one of the other sensory delivery systems. By example, the pumps or valves to the containers can be activated in response to an audio activated controller which uses audio signals or tones to activate the pumps or valves.

The fan assembly draws ambient air 119 into an isolated section of the housing 26 and directs it exteriorly of the primary optical chamber to the throat of the venturi 112 where essence oils are entrained by venturi action into the air stream. The air stream passes through the venturi into the viewing chamber 68 and across the viewport 38 to the exhaust outlet 46 formed in the viewport mask 40. The air with the aromatics entrained therein is thereafter directed through the filter assembly 48 as previously described before being exhausted to atmosphere through the exhaust opening 50.

Each aromatic exhaust tube 108 is connected to a spring loaded valve such that the valve closes when no pressurized air flows through the connected exhaust tube. It should be noted as shown in FIG. 7 that the orientation of the exhaust tubes 108 is such that a vertical component is maintained along the full length of the tube so that any aromatics are essences which may condense along the length of the tube will drain by gravity back into the containers 100 thus preventing contamination of the injector valves 110. The rate of air flow through the venturi 112 may be controlled by operation of the fan assembly 116 to thereby vary the olfactory stimulation for a person who is utilizing the multisensory stimulation apparatus of the invention.

Although not shown in the drawing figures, a removable panel may be provided in the housing 26 which can be removed to gain access to the pump 105 and the distribution header 104. A panel 122 permits access to the containers 100 such that changes may be made with respect to the various aromatics which are being dispensed therefrom.

A schematic of the operational characteristics of the aromatic sensory delivery system is shown in block diagram in FIG. 8. The aroma controller is electrically connected to the air pump 105 and to the distribution header 104 which includes the valves for selectively opening the aroma inlet conduits 102 to the essence bottles 100. By selecting the proper inlets 102 different essences can be entrained within the pressurized air which flows from the air pump 105 through the header 104. Thereafter, the aromatic air passes through the discharge conduits 108 through the injection valves 110 into the venturi 112 where the aromatics or essences are entrained within the circulation air flow which has been filtered in the filter 115 with the air being drawn by the fan assembly 116. The air then passes to the viewing chamber 68 where the aromas are made available in the area of the viewport 38 before being discharged through the discharge outlet 46 and filtered at 48 before being discharged atmosphere at 50. A fan flow controller 201 controls the operation and speed of the fan assembly 116 and therefore the rate of air flow through the viewing chamber.

Figure 9:
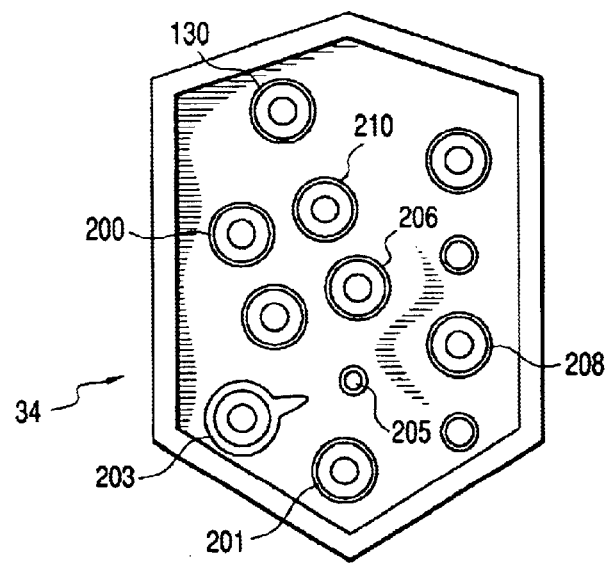
FIG. 9 is a front plan view of a control panel used in accordance with the invention.

With particular reference to FIG. 9, one configuration of control panel 34 of the present invention is shown in greater detail. The control panel 34 is strategically placed along the back panel 35 of the housing 26 as shown in FIG. 1. The panel includes a master power switch 130 which, when in an "ON" position also activates the cooling fan or fans 74 for the monitoring display. A separate switch 200 is used to activate aroma controller 245, which in the embodiment shown, is an audio tone controller, which in turn controls the aroma pump 105 and the valves of the distribution header 104. Air into the viewing chamber is provided by actuation of switch 201 which controls the inlet fan assembly 116 as well as the exhaust fan 49 which discharges filtered air through exit port 50. The rate of air flow through the venturi is controlled by an adjustment knob 203 which thus regulates the operating speed of the fan assembly 116 and the discharge fan 49.

An input port 205 is provided to switch the internal monitor 60 on and off, and to change its built-in settings, such as by use of an infrared remote control. Switch 206 is provided for enabling or disabling the servo or solenoid 96 which operates or opens the shutter 94 and simultaneously activates the blacklight source 92 to supply blacklight into the secondary optics tunnel 90. Switch 208 is provided for enabling or disabling the strobe light apparatus 100.

As previously discussed, in addition to the primary sensory stimulation systems of the invention including the visual, audio and aromatic, the present invention also may include either a heating, cooling or vibrational component which is affiliated with the chair or seating device 25. In FIG. 9, switch 210 is provided which is electrically connected to multiple transducers 212 and/or heat exchange devices such as heating or cooling elements 213 mounted within the cushioning and armrests of the seat or chair 25.

Audio, video and other and control signals are carried through a cable harness which extends up through the base into the housing 26, and then are distributed throughout the machine via a wiring harness, similar to those in an automobile, to the proper device or controller.

The control panel shown in FIG. 9 is generally used for manual system enabling or activation, however, an appropriate computer may be used with the system of the present invention. The computer may be electrically connected to each of the primary working components of the system including the monitor 60, the secondary light source shutter controller 96 and the blacklight source 92, the secondary light source strobe 100 and to the airflow fans for use with the aromatic sensory delivery system including the controller switch 201 connected to the exhaust fan 49 and the intake fan assembly 116, and the controller 245 for the pump 105 and the distribution header 104 associated with the aromatic containers 100. The computer may also be connected to automatically control operation of the chair vibrators 212 or heat exchange devices 213 associated with the chair and may be connected to an audio input system which may be a DVD player or the like which is connected to power the speakers 42 or headphones by way of which sound is transmitted to a person experiencing the multisensory stimulation. The computer may also be connected to any type of video programming device to control the programming of the device such as by selection of a particular track of a DVD system to provide images to the monitor 60.

Figure 10:
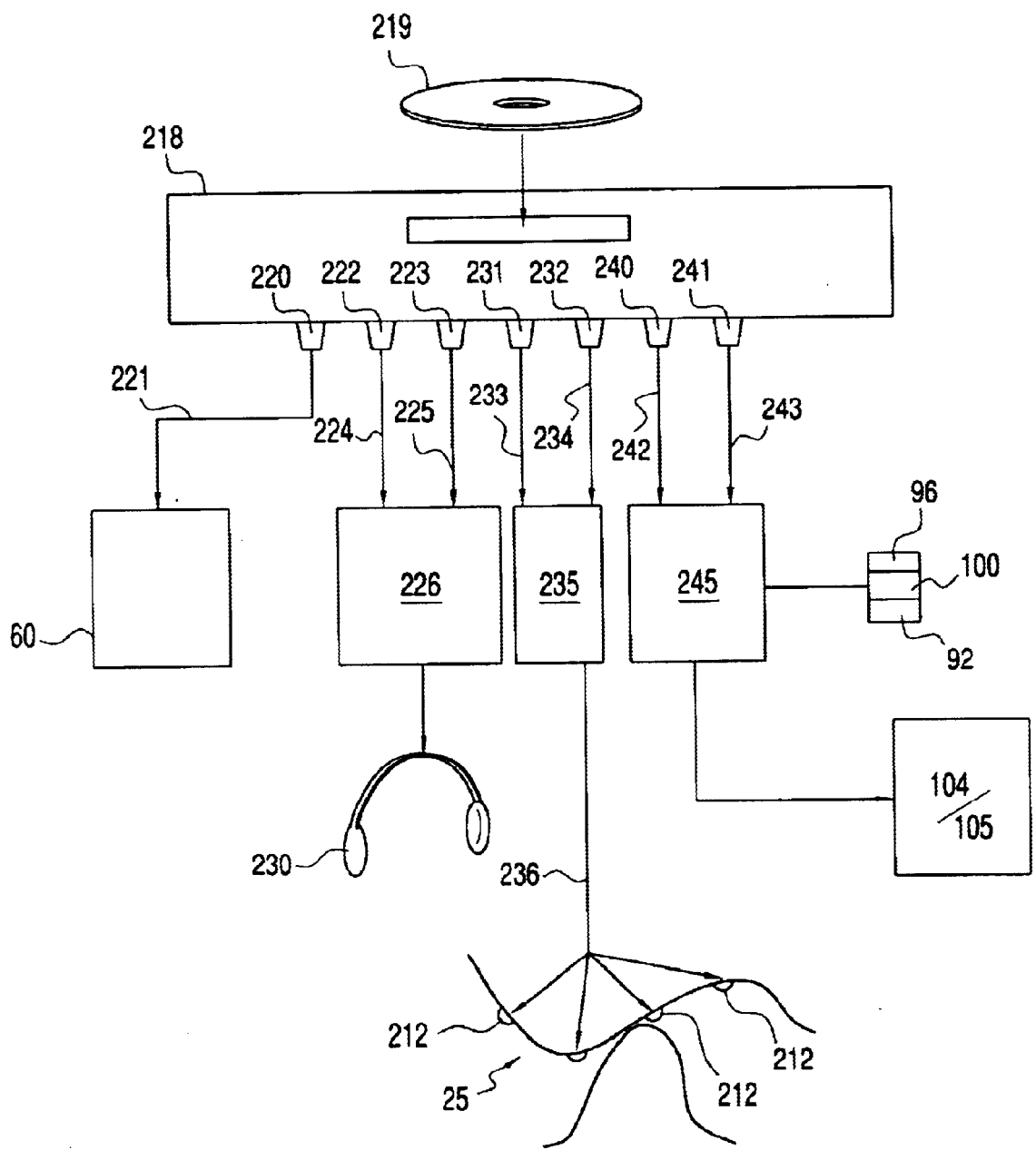
FIG. 10 is an illustration diagram of a non-interactive control system of the invention.

With respect to FIG. 10, an illustrational diagram is shown with respect to the operating and control components of one form of non-interactive embodiment of the invention. In this embodiment a computer or computer-like device can be used to provide program control to the various sensory stimulation input systems of the invention. As illustrated, the computer-like device is in the form of a DVD player 218 which receives a program disk 219 with video and encoded digital surround sound signals (Dolby™ or DTS).

The DVD player includes a built-in decoder for processing the surround sound, either Dolby™ Digital or DTS. In the illustration, the DVD player includes a first video output 220 which is connected by way of cable 221 to the video monitor 60 associated with the invention. The left and right sound outputs 222 and 223 are connected through cables 224 and 225 to a headphone amplifier 226 which may be mounted within the housing 26 of the invention, or adjacent thereto, and to which is connected binaural audio headphones 230. As opposed to using the headphones 230, the speakers 42 built into the housing may be connected to the amplifier 226.

Utilizing additional auxiliary outputs from the DVD player, the transducers 212 mounted to the chair 25, or the heat exchange elements 213 associated with the chair, may be controlled, and in like manner, so can the secondary or blacklight and strobe light sources and aroma system of the present invention.

As shown in FIG. 10, outputs 231 and 232 from the DVD player are connected through cables 233 and 234 respectively to a stereo audio amplifier 235 which may be mounted within the housing 26 or adjacent thereto. The stereo audio amplifier is electrically connected through cables 236 to the transducers 212 of the chair 25 and may also be connected to the heat exchangers 213.

In addition to the foregoing, additional analog line outputs 240 and 241 of the DVD player may be connected through cables 242 and 243, respectively, to the aroma controller 245. The controller 245 is not only connected to the aroma control system but is also connected to control the various light and shutter mechanisms of the present invention. In the illustration, the controller 245 is a tone controller which converts the sound signals received from the DVD player into electrical pulses for controlling the strobing of the strobe light 100. Although not specifically shown, the controller may be separately connected to the shutter mechanism 96 and to the blacklight 92 of the invention. Further, the controller is connected to the pump and valves 105 and 104 of the aroma system of the present invention, such that aroma is supplied depending upon audio signals received at the controller.

In accordance with the non-interactive embodiment of the invention as shown in FIG. 10, it can be seen that a very simple computer-like device, such as a DVD player, can be utilized to receive DVD program disks in order to create and control signals going to each of the sensory stimulation systems of the invention. The use of the DVD player can be regulated in accordance with other controls of the control panel shown in FIG. 9 to create further variations in sensory stimulation.

The generally non-interactive embodiment of the invention disclosed in FIG. 10 may be modified to allow a person undergoing therapy to become interactive to vary the sensory stimulation developed by each of the systems of the present invention. By way of example, and as previously noted, a microphone 44 is incorporated with the soft mask of the invention such that a person seated within the chair 25 can communicate to a computer-like device in order to effect the programming and input to the sensory systems.

Figure 11:
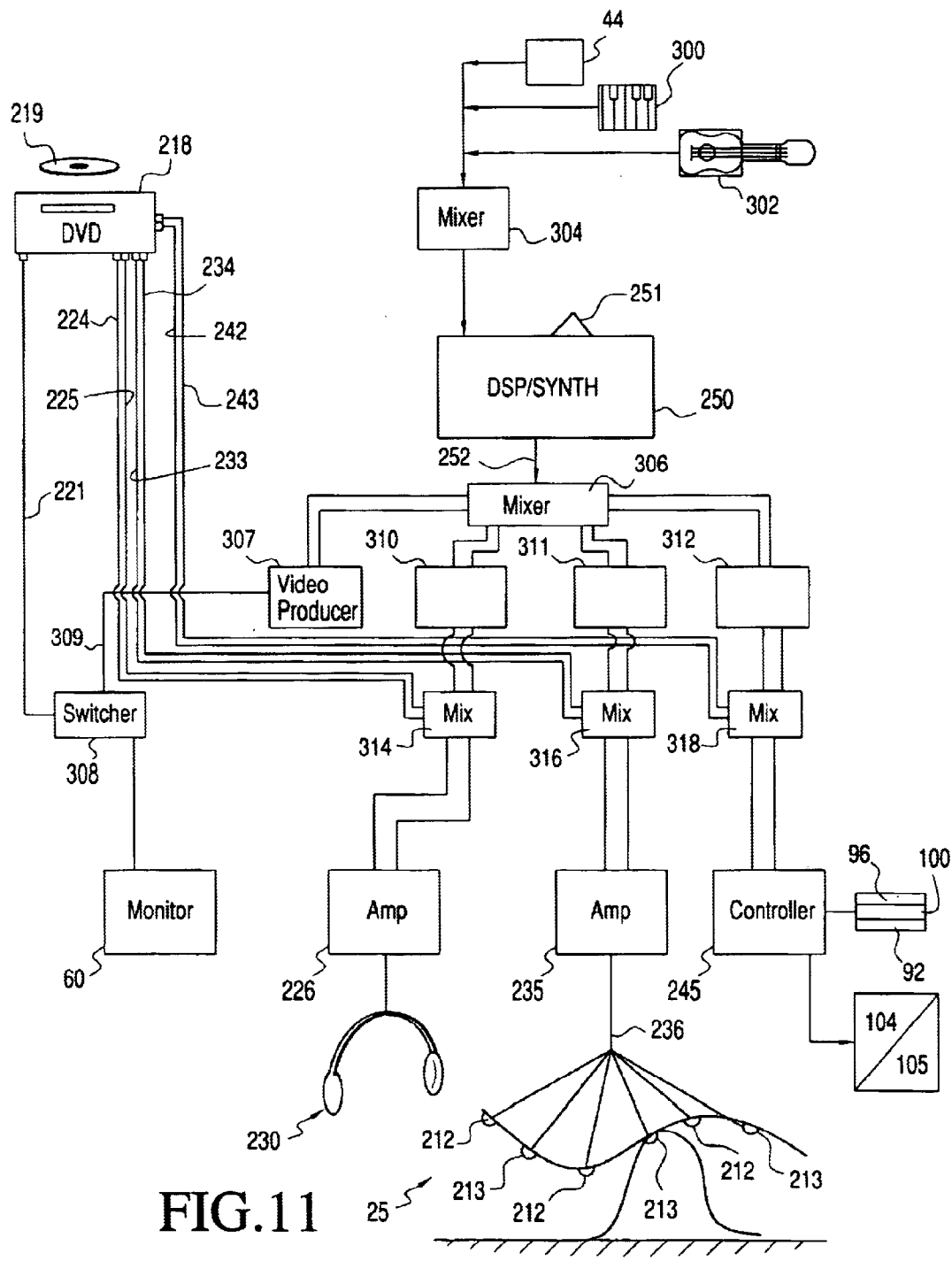
FIG. 11 is a diagram of a modification to the control system of FIG. 10 allowing interaction.

With particular reference to FIG. 11, an illustrational diagram is shown with respect an alternative embodiment of operating and control system of an interactive type in accordance with the teachings of the invention. In this embodiment, one or more audio inputs can be selectively connected to a computer-like device such as a DSP (digital signal processor) and synthesizer 250. As shown, the microphone 44 is connected to the DSP/synthesizer 250 by way of a pre-amp mixer 304. As opposed to a microphone or in addition thereto, other types of audio inputs can be electrically connected to provide either digital or analog signals as inputs to the DSP/synthesizer 250. As illustrated in the drawing figure, an electronic keyboard 300 or electronic musical instrument, such as a guitar 302, maybe used to generate audio outputs which are supplied to the DSP/synthesizer 250 by way of the pre-amp mixer 304.

In a preferred embodiment, the DSP/synthesizer 250 is an "airFX"™ device which is essentially two instruments in one functioning both as a synthesizer and as a DSP. Both the synthesizer and the DSP take control commands from an infrared device 251 which is similar in function to a keyboard or other input device such as a game joystick. By an individual moving a hand over the infrared device, changes are made in the input signals to the DSP/synthesizer and, thereby, changes are made in the output 252 from the DSP/synthesizer. In effect, the infrared device tells the DSP/synthesizer what to play when the DSP/synthesizer is an synthesizer mode. When the DSP/synthesizer is in a DSP mode the infrared device controls the internal DSP to modify sounds which are inputted into it from the pre-amp mixer 304. The "airFX"™ is a device manufactured by Alesis.

The output signals 252 from the DSP/synthesizer are fed to the amplifiers 226, 235 and controller 245. The amplifier 226 provides signals to the headphones 230 whereas the amplifier 235 is connected as described with respect to the embodiment shown in FIG. 10 to the transducers 212 and/or heat exchange elements 213 associated with the chair 25. Controller 245 provides signals to control the secondary optical assembly including the shutter actuation member 96, the blacklight 92 and the strobe assembly 100. In addition, the controller 245 provides input to the pump 105 and valves 104 of the aroma system of the invention such that aroma is supplied depending upon audio signals received at the controller.

As shown, the DSP/synthesizer 250 provides the output signal 252 preferably into a mixer 306 which is connected to provide signals to a video processor 307 connected to a video switcher 308 which supplies an output signal to the video monitor 60. In a similar manner, the mixer 306 is connected to provide output to a plurality of special "effect boxes" 310, 311 and 312. The special effect boxes are added to the system to adjust any of the output signals from the mixer 306 as desired. For example, the effect box 310 may be used to change signals to increase or decrease sound reverberation or to change treble and base frequencies as desired. Further, the signals can be changed to create echoes or to change the sound to an acoustics of concert hall or other room as is well known in the art. The signals from the "effect boxes" 310, 311 and 312 are thereafter inputted to the amplifiers and controller 226, 235 and 245.

As previously noted, in this embodiment of the invention, the non-interactive embodiment of the invention disclosed in FIG. 10 may be modified allowing a person undergoing therapy to become interactive to vary the sensory stimulation signals developed by the systems of the invention. In this respect, and as shown in FIG. 11, signals from a computer-like device, such as the DVD player 218 of FIG. 10, can be mixed with the signals coming from the DSP/synthesizer 250. As shown, the output signals from the DVD player can be used to modify the signals coming from the DSP/synthesizer 250 before the signals reach the monitor, the amplifiers or the controller as previously described. The DVD player is shown as being connected through line 221 to the video switcher 308 to thereby vary the output signal therefrom to monitor 60. The outputs 224 and 225 are shown as being connected to a mixer 314 which receives input signals from the processing and effects box 310. The outputs 233 and 234 from the DVD player 218 are connected to a mixer 316 to modify the signal coming from the effect box 311. Further, the outputs 242 and 243 of the DVD player are shown as being connected to a mixer 318 which is used to vary the signals coming from the effect box 312 before the signals are passed to the controller 245.

The mixers can be used to combine and adjust levels of audio and video signals as is desired. The mixers can be used at any point along the signal chain in order to join separate signal streams together to thereby modify the final input into the amplifiers and controllers of the invention. The video signal of the embodiment shown in FIG. 11 is processed at the video processor 307 such as by utilizing an "Eye Candy" computer program. The output from the video processor is thereafter fed to the video switcher 308 where the input signals from the DVD player 218 are used to modify the signals further before the signals are passed to the monitor. In this manner, the output from the video processor is mixed with the video from the DVD player, when desired, so as to create optional video effects such as providing picture-in-picture effects, transparent overlays and the like at the monitor 60.

It should be noted that the functioning of each of the elements described in FIG. 11 can be accomplished by a dedicated computer workstation with appropriate software and related audio hardware.

In the foregoing manner, a person using the microphone can use their own voice to alter the effects of the sensory inputs to both the visual, audio, olfactory, tactile and sensory input systems of the invention.

With specific reference to FIG. 12, an illustrative diagram of another embodiment of the operating and control system of the invention is disclosed which is designed to provide for complete interactive control of the sensory stimulation systems by a person undergoing treatment or therapy. The interactive system includes the use of biofeedback sensors and possibly a voice recognition system as well as various other input devices to both subconsciously and consciously manipulate or alter the programmed control of the sensory stimulation system. Programmed Control may be accomplished by utilization of one or more available generic or proprietary interactive multimedia systems, virtual reality systems, or game systems, which with associated computers, media synthesizers, media processors and players and the like, provide output to the delivery systems by way of conventional adapters or interfaces. Further, such program control systems can generate real-time or access stored data which can be maintained as libraries and available either locally or remotely and made available such as over the internet.

One of the unique features of the interactive system of the present invention is that it can be set up to allow for subconscious as well as conscious intervention on the part of a person undergoing treatment or therapy. As shown in the drawing figures, subconscious control is provided through biofeedback and other sensors which are utilized to supply information to a processor 260. The subconscious biofeedback and other sensors are generically shown as being connected through an input 261. Such sensors not only reflect the subconscious mind of the person but also the physical conditions of the individual's body.

The interactive system of FIG. 12 may also include conscious input signals, such as through an input 263 to the processor 260, which inputs are connected to devices which can be manipulated by the person, such devices may reflect responses to various senses being stimulated as well as to a subject's preferences and/or choices as experienced during treatment or therapy. Such conscious control devices are generally identified at 265 and may include, but are not limited to, signals received by voice command such as through the microphone 44 as discussed with respect to FIG. 11, hand manipulation devices including squishy gelpads, joysticks, trackballs, mouses, MIDI controllers including keyboards, drumpads, breath and infrared devices, motion trackers, including infrared devices, dataGloves and the like.

In the present embodiment, additional control over the sensory stimulation program is permitted by the operator "O" who controls the processor 260 through an input 266 from a computer device 267. The operator can monitor the program on the computer 267 in order to evaluate and/or intervene in the control of the sensory systems of the present invention depending upon the input received from components of the system.

In a preferred embodiment, the processor 260 may be utilized to develop a profile or personal library with respect to each person undergoing therapy. A the profile or personal library 268 is shown as being connected to the processor 260 and such library may contain information specific to control of the sensory systems of the present invention which are individualized to a person undergoing treatment or therapy.

As shown further in FIG. 12, the processor 260 may be connected to an interactive media controller 270 which may be designed to allow control using pre-prepared software programs. The multimedia controller 270 is connected to a plurality of media processors and/or players, media synthesizers and media databases 271, 272, and 273. The media processors and players 271 may include multimedia playback systems and/or multimedia storage or playback devices which are available locally or over a network. Such devices may include hard drives, DVD, DVD-ROM and CD-ROM drives, VCRs, tape players, hi-fi audio equipment, multi-track audio cards, MIDI and synthesizer-type playback devices, dual monitor video cards and even film projection devices. The media processors and players may also include media mixers, routers and switches, DSPs, converters and amplifiers to combine, modify, transform, alter or adjust any media signal or format for final media output. By way of example, the processors and players can manipulate existing files from the media program database. In this manner changes can be made such as adjusting the volume or adding reverb or echoes to recorded sound files, reversing the color output in video, lightening or darkening existing or generated images, combining two images together on one screen, etc.

The media synthesizers 272 may include real-time devices which are used to generate new or original media files such as sounds, images and other signals for file control and display. These may include systems such as music synthesizers responding to a hand on a keyboard, or fractal images being created by biological inputs altering a mathematical formula that structures a creation, or a virtual reality simulation generated by a wave of the hand causing the user to float through an abstract world of colors, light and sound. The media database 273 may include a software library which can contain databases containing moving or still images, color palettes, fonts, symbols, words and music, tones and vibrations, aroma control sequences, MIDI control data, mathematical formulas, specifications, texture maps and other information which is pre-prepared for altering the file output from the interactive media controller 270. The media database 273 contains the raw material or building blocks for the various media players and processors 271 and the media synthesizers 272 to store, present or play back, refashion, assemble, alter, base new content upon, generate totally or in part from, or manipulate as directed by the interactive media controller 270 or other controller or program.

As shown, the output from the interactive media controller is connected through a plurality of outputs 281, 282, 283 and 284 to the various sensory input systems of the invention. As shown, output 281 can be utilized to control the transducers 212 associated with the seat 25 of the invention, whereas the output 282 may be connected to control audio output. Output 283 may be connected to the primary and secondary optic systems of the invention while output 284 may be connected to the aroma control system of the invention.

In addition to the foregoing, an output 285 from the interactive multimedia controller 270 may be connected directly to the operator's computer 267 to allow continuous monitoring of the treatment or therapy.

As previously noted, it may be beneficial to establish a subject profile or personal library to monitor and to control treatment and therapy. Such a profile or personal library may be developed in response to previous treatments, monitoring an individual's response to current treatment, establishing likes and dislikes by questions and answers prior to undergoing therapy or treatment and the like. It is preferred, however, to develop the personal library or profile of an individual so that it is possible to avoid possible problems, such as possible adverse responses due to allergies, subject's sensitivities, such as to audio volumes and light levels, or conditions which could have a possible adverse effect on an individual undergoing therapy or treatment.

In view of the foregoing, the multisensory stimulation system of the present invention allows a person to experience individualized programs of varied stimulation elements including audio, visual, olfactory, tactile and the like wherein the stimulation may be varied to enhance responses. Further, individual profiles or libraries can be created so that programs can be uniquely configured for facilitating treatment and/or therapy.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims and their equivalents.

We claim:

1. A multisensory stimulation system including a housing having a view port, a primary optical assembly having a primary reflective chamber mounted within said housing defined by a plurality of inner reflective surfaces, a viewing chamber communicating through a first opening to said primary reflective chamber, a viewport communicating with said viewing chamber so as to allow images and light therein to be observed therethrough, a first sensory input means including a projection source mounted adjacent to said primary reflective chamber for projecting light and images into said primary reflective chamber through a second opening spaced from said viewport, first control means for controlling said first sensory input means, a second sensory input means carried by said housing, said second sensory input means including an aromatic delivery means, said aromatic delivery means including a plurality of essence containers, a source of pressurized air, means for selectively connecting said source of pressurized air with said plurality of essence containers to thereby entrain essences in said pressurized air, a venturi passageway positioned to communicate said aromatic delivery means with said viewing chamber, means for conveying pressurized air with at least one essence entrained therein to said venturi passageway, a ventilation system for introducing an airflow through said venturi passageway toward said viewing chamber, means for introducing said pressurized air with at least one entrained essence into said airflow through said venturi passageway, and second control means for controlling said means for selectively connecting said source of pressurized air with said essence containers to control which essence containers communicate with said pressurized air whereby visual and olfactory senses can be selectively stimulated by said first and second sensory input means.

2. The multisensory stimulation system of claim 1 including a third sensory input means, said third sensory input means including an audio output means connected to an audio input means, and third control means for controlling an audio input to said audio output means.

3. The multisensory stimulation system of claim 1 including a secondary optical assembly including a secondary reflective chamber, said secondary reflective chamber being mounted adjacent a third opening into said primary reflective chamber, said secondary reflective chamber including a reflective tunnel having a first opening in communication with said projection source of said first sensory input means and a second opening communicating with said third opening into said primary reflective chamber whereby light and images from said first sensory input means reflected through said reflective tunnel enters said primary reflective chamber.

4. The multisensory stimulation system of claim 3 in which said reflective tunnel includes a shutter, means for moving said shutter between opened and closed positions across a third opening into said reflective tunnel, a secondary light source means mounted adjacent to said shutter and being communicated with said reflective tunnel when said shutter is in said opened position, and fourth control means being connected with said shutter to control movement of said shutter between said opened and said closed positions.

5. The multisensory stimulation system of the claim 4 in which said secondary light source includes a black light source, flourescent surface coatings provided on said inner reflective surfaces of said primary reflection chamber, said flourescent surface coatings being illuminated by said black light source when said shutter is in said opened position.

6. The multisensory stimulation chamber of claim 5 including a strobe light system, means for communication said strobe light system through said third opening into said secondary reflective tunnel when said shutter is in said opened position, and means for operating said strobe light system.

7. The multisensory stimulation system of claim 3 in which a Fresnel lens is mounted between said second opening in said reflective tunnel and said third opening into said primary reflective chamber.

8. The multisensory stimulation system of claim 3 in which said projection source of said first sensory input means includes a video monitor mounted within said housing, said video monitor having a display screen having a first portion communicating with said primary reflective chamber and at least one second portion communicating with said reflective tunnel thereby portions of images radiated by said video monitor are directed directly into said primary reflective chamber and other portions of the images are directed through said reflective tunnel to said primary reflective chamber.

9. The multisensory stimulation system of claim 8 including a fan means mounted adjacent to said video monitor, means for drawing air through said housing and adjacent to said video monitor and exhausting said air to atmosphere.

10. The multisensory stimulation system of claim 1 including means adjacent said viewport for exhausting said airflow from said viewing chamber through an outlet filter before being discharged to atmosphere.

11. The multisensory stimulation system of claim 1 in which said viewport is surrounded by a soft protective mask adapted to reduce outside interferences.

12. The multisensory stimulation system of claim 1 in which said primary reflective chamber is in a general form of a rhombic dodecahedron.

13. The multisensory stimulation chamber of claim 1 in which said housing is mounted on a stand, means for pivotally mounting said housing to said stand so as to be rotational about a vertical axis such that said housing may be adjusted relative to an individual.

14. The multisensory stimulation system of claim 13 including a seating device mounted adjacent said stand for said housing.

15. The multisensory stimulation system of claim 14 including means for vertically adjusting a height of said housing relative to said seating device.

16. The multisensory stimulation system of claim 2 including a control panel mounted to an outer portion of said housing, said control panel being electrically connected to said first, second and third control means.

17. The multisensory stimulation system of claim 1 in which said second sensory input means includes a fluid header mounted between said source of pressurized air and said essence containers, a plurality of valves for controlling output from said header so as to selectively connect said pressurized source of air with selected essence containers.

18. The multisensory stimulation system of claim 14 including tactile stimulation means mounted to said seating device, and means for controlling activation of said tactile stimulation means.

19. The multisensory stimulation system of claim 2 in which said audio output means includes audio speakers mounted adjacent said view port.

20. The multisensory stimulation system of claim 2 in which said audio output means includes headphones selectively connected to said audio input means.

21. The multisensory stimulation system of claim 2 including a processor means, means for connecting said processor means to said first, second and third control means.

22. The multisensory stimulation system of claim 21 including microphone means, means for connecting said microphone means to said processor means such that voice commands received at said microphone means may be used to control said first, second and third control means.

23. The multisensory stimulation system of claim 21 including at least one bio-feedback sensor connected to said processor means for monitoring an individual undergoing sensory stimulation such that bio-feedback signals may be used to control said first, second and third control means.

24. The multisensory stimulation system of claim 23 in which said at least one bio-feedback sensor is selected from a group of sensors consisting of EEG or brainwave monitor, heart rate monitor, breathing monitor, body temperature sensor, galvanic skin response sensor, voice recognition sensor analyzer, and eye tracking movement or dilation sensor.

25. The multisensory stimulation system of claim 21 including manually manipulative input means connected to said processor means, said manipulative input means being selectively activated by a person undergoing sensory stimulation to provide conscious input into said processor means.

26. The multisensory stimulation system of claim 2 including a media player for playing a media recorded on a disk, and means for connecting said media player to said first, second and third control means.

27. A method of providing multisensory stimulation to an individual using a system including a housing which is mounted adjacent a seating device on which an individual may be seated and wherein the housing defines a viewing chamber in which images from an image projection means are reflected to a viewport so as to be viewable by an individual seated in the seating device and wherein the housing further includes an aromatic essence delivery system by way of which selected essences may be injected into an air flow directed toward said viewport and wherein an audio output means is provided for creating sounds which may be heard by an individual seated in the seating device and wherein the device further includes control means for controlling activation of the image projection means, the aromatic essence delivery system and the audio output means, the method comprising:

A. aligning the housing such that the individual's face is positioned within the viewport having an opening sized so that at least the individual's eyes and nose are in direct communication with the viewing chamber and are blocked from ambient visual and olfactory conditions;

B. providing an output signal from the control means for controlling the activation of the image projection means, aromatic essence delivery system and audio output means depended upon a predetermined media program; and C. varying the output signal to the image projection means, essence delivery system and audio output means depending upon input received from an individual seated in the seating device.

28. The method of claim 27 including the additional step of providing at least one bio-feedback sensor and placing the bio-feedback sensor so as to generate a signal relative to at least one physical characteristic of an individual seated within the seating device and altering the output signal to the control means for the image projection means, aromatic essence delivery system and audio output means with said bio-feedback signal.

29. A multisensory stimulation system including a housing having a viewport having an opening sized of a size to receive a person's face so that at least the person's eyes and nose are blocked from ambient conditions, a primary optical assembly mounted within said housing including a primary reflective chamber defined by a plurality of intersecting and angularly related inner reflective surfaces and a first sensory input means including a light and image projection source mounted to project images into said primary reflective chamber so that each image, after reflecting on said plurality of inner reflective surfaces, is simultaneously viewed through said viewport as a plurality of reflected images, said housing being adjustably mounted on a base, a seating device positioned adjacent said base such that said housing may be adjusted and positioned relative to said seating device to thereby accommodate an individual seated on said seating device and means for controlling said light and image projection source to vary images projected into said primary reflective chamber.

30. The multisensory stimulation system of claim 29 including a second sensory input means mounted within said housing and including an aromatic delivery means, said aromatic delivery means including a plurality of essence containers mounted within said housing and a source of pressurized air for distributing essences from selected containers through a plurality of conduits to a plurality of valves positioned adjacent said viewport, so that said plurality of conduits and valves are operable to reduce cross contamination between different essences.

31. The multisensory stimulation system of claim 30 including a third sensory input means including an audio input means mounted within said housing and a fourth sensory input means including tactile means associated with said seating device and means for controlling said third and fourth sensory input means.

32. The multisensory stimulation system of claim 30 including a secondary optical assembly having a secondary reflective chamber having a plurality of reflective surfaces for directing images from said light and image projection source into said primary reflective chamber through a lens member.

* * * * *